(12) United States Patent
Afzali-Ardakani et al.

(10) Patent No.: US 8,598,569 B2
(45) Date of Patent: Dec. 3, 2013

(54) PENTACENE-CARBON NANOTUBE COMPOSITE, METHOD OF FORMING THE COMPOSITE, AND SEMICONDUCTOR DEVICE INCLUDING THE COMPOSITE

(75) Inventors: Ali Afzali-Ardakani, Ossining, NY (US); Cherie R. Kagan, Bala-Cynwyd, PA (US); Rudolf M. Tromp, North Salem, NY (US)

(73) Assignee: International Business Machines Corporation, Armonk, NY (US)

( * ) Notice: Subject to any disclaimer, the term of this patent is extended or adjusted under 35 U.S.C. 154(b) by 717 days.

(21) Appl. No.: 12/113,064

(22) Filed: Apr. 30, 2008

(65) Prior Publication Data
US 2009/0272967 A1 Nov. 5, 2009

(51) Int. Cl.
*H01L 29/08* (2006.01)
*H01L 35/24* (2006.01)
*H01L 51/00* (2006.01)

(52) U.S. Cl.
USPC ...... 257/40; 438/99; 423/447.1; 257/E21.001

(58) Field of Classification Search
USPC ............... 423/447.1, 445 B; 257/40, 257/E51.001–E51.052; 438/99
See application file for complete search history.

(56) References Cited

U.S. PATENT DOCUMENTS

| | | | |
|---|---|---|---|
| 6,963,080 B2 | 11/2005 | Afzali-Ardakani et al. | |
| 7,125,989 B2 | 10/2006 | Afzali-Ardakani et al. | |
| 2004/0183070 A1 | 9/2004 | Afzali-Ardakani et al. | |
| 2005/0061451 A1 | 3/2005 | Busnaina et al. | |
| 2005/0287717 A1 | 12/2005 | Heald et al. | |
| 2006/0105513 A1 | 5/2006 | Afzali-Ardakani et al. | |
| 2006/0151844 A1 | 7/2006 | Avouris et al. | |
| 2006/0165896 A1 | 7/2006 | Afzali-Ardakani et al. | |
| 2007/0029600 A1 | 2/2007 | Cohen | |
| 2008/0102213 A1 | 5/2008 | Afzali-Ardakani et al. | |

FOREIGN PATENT DOCUMENTS

WO WO 2007/074339 A1 7/2007
WO WO 2008/011623 A2 1/2008

OTHER PUBLICATIONS

Cao et al., "Transparent flexible organic thin-film transitors that use printed single walled carbon nanotube electrodes", Applied Physics Letters 88, p. 113511, 2006.*
Tsukagoshi et al., "Pentacene nanotransistor with carbon nanotube electrodes", Applied Physics Letters, vol. 85, No. 6, 2004 pp. 1021-1023.*
Chemistry, Seventh Edition, Chang, McGraw-Hill Companies, 2002 pp. 419-421.*
Gotovac et al. "Effect of Nanoscale Curvature of Single-Walled Carbon Nanotubes on Adsorption of Polycyclic Aromatic Hydrocarbons", Nano Letters, 2007, vol. 7, No. 3, pp. 583-587.*
Klarner et al., "Synthesis and supramolecular structures of molecular clips", Tetrahedron, vol. 57 (2001), pp. 3673-3687.*

(Continued)

*Primary Examiner* — Julio J Maldonado
*Assistant Examiner* — Sonya D McCall Shepard
(74) *Attorney, Agent, or Firm* — Vazken Alexanian; McGinn IP Law Group, PLLC

(57) ABSTRACT

A composite material includes a carbon nanotube, and plural pentacene molecules bonded to the carbon nanotube. A method of forming the composite layer, includes depositing on a substrate a dispersion of soluble pentacene precursor and carbon nanotubes, heating the dispersion to remove solvent from the dispersion, heating the substrate to convert the pentacene precursor to pentacene and form the carbon nanotube-pentacene composite layer.

16 Claims, 6 Drawing Sheets

(56) References Cited

OTHER PUBLICATIONS

Tromp et al. Novel Strategy for Diamter-Selective Separation and Functionalization of Single-Wall Carbon Nanotubes, Nano Letters 2008, vol. 8, No. 2, pp. 469-472.*

PCT Written Opinion of the International Searching Authority.

Bo, et al., "Pentacene-Carbon Nanotubes: Semiconducting Assemblies for Thin-Film Transistor Applications", Applied Physics Letters, AIP, American Institute of Physics, Melville, NY, US, vol. 87, No. 20, Nov. 10, 2005, pp. 203510-1-203510-3.

United States Office Action dated Aug. 17, 2011 in U.S. Appl. No. 12/195,524.

United States Office Action dated Jan. 11, 2012, in U.S. Appl. No. 13/077,216.

United States Office Action dated Jun. 1, 2012, in U.S. Appl. No. 13/077,216.

United States Office Action dated Sep. 10, 2013, in U.S. Appl. No. 13/617,420.

* cited by examiner

Where:

=

PENTACENE-CARBON NANOTUBE COMPOSITE, METHOD OF FORMING THE COMPOSITE, AND SEMICONDUCTOR DEVICE INCLUDING THE COMPOSITE

BACKGROUND OF THE INVENTION

1. Field of the Invention

The present invention relates to a composite material which includes a carbon nanotube, and plural pentacene molecules bonded to the carbon nanotube, and more particularly, to a method of forming a semiconductor device including forming a channel region which includes a carbon nanotube-pentacene composite layer.

2. Description of the Related Art

Organic semiconductors have been studied extensively for use as channel materials in thin film transistors. In particular, solution processed pentacene thin film transistors (TFT) have been formed using soluble pentacene precursors which after deposition on the surface could be converted to pentacene by moderate heating. For example, see U.S. Pat. No. 6,963,080 to Afzali-Ardakani et al. entitled "THIN FILM TRANSISTORS USING SOLUTION PROCESSED PENTACENE PRECURSOR AS ORGANIC SEMICONDUCTOR", and U.S. Pat. No. 7,125,989 to Afzali-Ardakani et al. entitled "HETERO DIELS-ALDER ADDUCTS OF PENTACENE AS SOLUBLE PRECURSORS OF PENTACENE", which are commonly assigned with the present application and incorporated by reference herein.

However, the charge carrier mobility of these organic thin film transistors (OFET) are limited and usually in the range of $10^{-2}$ cm$^2$/V·sec to $10^{-1}$ cm$^2$/V·sec.

On the other hand, carbon nanotubes have been demonstrated to have charge carrier mobility far superior to that of single crystal silicon but are very difficult to fabricate integrated circuits.

SUMMARY OF THE INVENTION

In view of the foregoing and other problems, disadvantages, and drawbacks of the aforementioned compositions, methods and devices, it is a purpose of the exemplary aspects of the present invention to provide, inter alia, a method of forming a semiconductor device including forming a channel region which includes a carbon nanotube-pentacene composite layer.

An exemplary aspect of the present invention is directed to a composite material including a carbon nanotube, and plural pentacene molecules bonded to the carbon nanotube.

Another exemplary aspect of the present invention is directed to a method of forming a carbon nanotube-pentacene composite layer. The method includes depositing on a substrate a dispersion of soluble pentacene precursor and carbon nanotubes, heating the dispersion to remove solvent from the dispersion; and heating the substrate to convert the pentacene precursor to pentacene and form the carbon nanotube-pentacene composite layer.

Another exemplary aspect of the present invention is directed to a field effect transistor which includes source, drain and gate electrodes formed on a substrate, and a channel region formed on the substrate, the channel region including a carbon nanotube-pentacene composite layer.

Still another exemplary aspect of the present invention is directed to a method of forming a field effect transistor. The method includes forming source, drain and gate electrodes on a substrate, and forming a channel region on the substrate, the channel region including a carbon nanotube-pentacene composite layer.

With its unique and novel features, the exemplary aspects of the present invention may provide a method of forming a semiconductor device including forming a channel region including a carbon nanotube-pentacene composite layer.

BRIEF DESCRIPTION OF THE DRAWINGS

The foregoing and other objects, aspects and advantages will be better understood from the following detailed description of the embodiments of the invention with reference to the drawings, in which.

DETAILED DESCRIPTION OF THE EXEMPLARY EMBODIMENTS OF THE INVENTION

Figure 1:
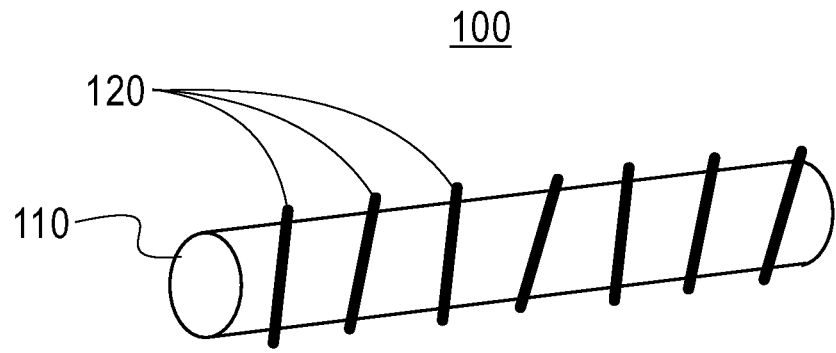
FIG. 1 illustrates a carbon nanotube-pentacene composite material 100, according to an exemplary aspect of the present invention.

Referring now to the drawings, FIGS. 1-6 illustrate the exemplary aspects of the present invention.

As illustrated in FIG. 1, the present invention includes a composite 100 (e.g., carbon nanotube (CNT)-pentacene composite) which includes a carbon nanotube 110, and plural pentacene molecules 120 bonded to the carbon nanotube.

The present invention may combine the superior transfer properties of carbon nanotubes with the ease of processing of organic semiconductors to obtain a semiconductor device (e.g., a field effect transistor) with much higher mobility than that of organic semiconductors by using a dispersion (e.g., a highly stable dispersion) of carbon nanotubes in solution of pentacene precursors in an organic solvent.

The carbon nanotube 110 may include, for example, an electrically semiconductive, single-walled nanotube (SWNT). The plural pentacene molecules 120 may interact strongly with the graphitic sidewall of the CNT and align on the sidewall of the CNT through π-π stacking (e.g., the rings of the pentacene molecules 120 may form a "stack" with the rings of the CNT). The molecules 120 may be bonded to the CNT 110, for example, by π-π bonding, charge transfer bonding and/or electrostatic bonding.

In particular, the pentacene may be bonded to (e.g., grafted to) the outer surface of the nanotube such that the double bonds of the CNT are essentially unaffected, thereby ensuring that the electrical and mechanical properties of the CNT are unaffected.

Figure 2:
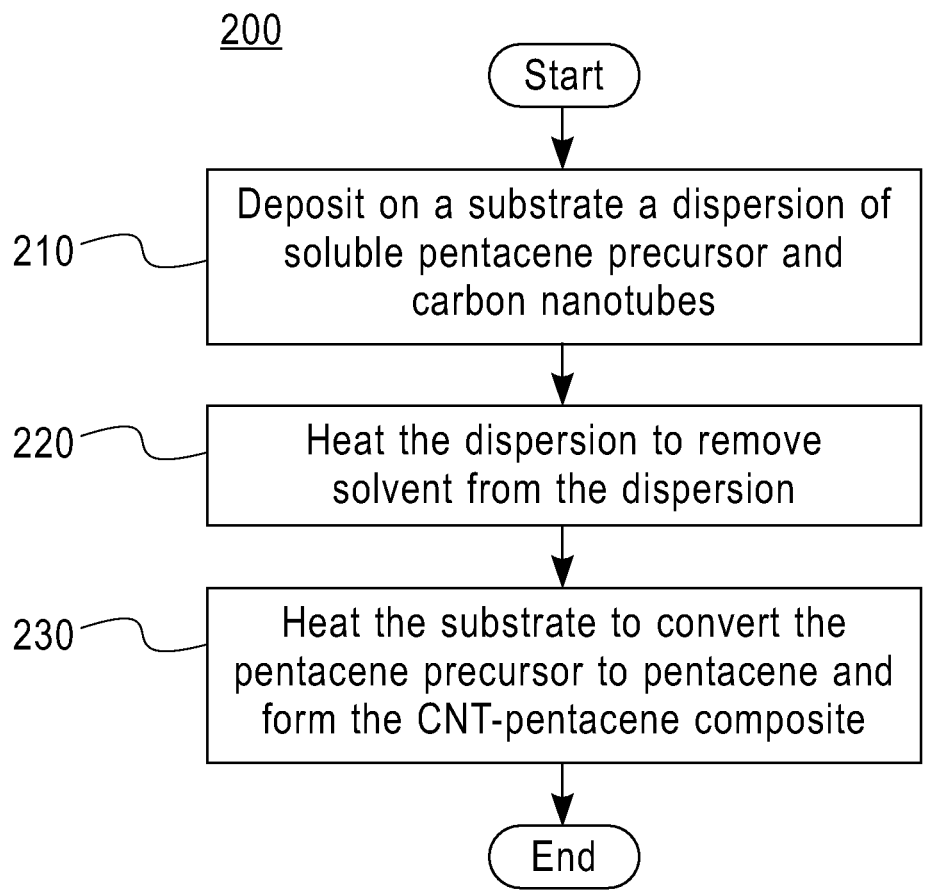
FIG. 2 illustrates a method 200 of forming the CNT-pentacene composite, according to another exemplary aspect of the present invention.

FIG. 2 illustrates a method 200 of forming the CNT-pentacene composite. The method 200 of forming the CNT-pentacene composite may include depositing (210) on a substrate a dispersion of soluble pentacene precursor and carbon nanotubes, heating (220) the dispersion (e.g., at a temperature in a range from 50° C. to 100° C.) to remove solvent from the dispersion, and heating (230) the substrate (e.g., at a temperature in a range from 100° C. to 200° C.) to convert the pentacene precursor to pentacene and form the CNT-pentacene composite.

Forming the Pentacene Precursor

The method 200 may also include reacting pentacene with a dienophile to form a pentacene precursor (e.g., a soluble pentacene precursor). It should be noted that although the present invention is described as including pentacene, other polycyclic aromatic compounds may also be used instead of pentacene.

The dienophile may include, for example, a compound that has at least one heteroatom such as N, O or S, connected by a double bond to a second heteroatom or carbon. In particular, the dienophile may include an N-sulfinylamide. For example, the dienophile may include N-sulfinyl acetamide.

The pentacene may be reacted with the dienophile at low to moderate temperatures and in the presence of a catalyst such as a Lewis acid catalyst to form the pentacene precursor. The Lewis acid catalyst may include, for example, titanium tetrachloride, silver tetrafluoroborate and methyl rhenium trioxide. Any residue from the dienophile remaining in the product of the reaction may be removed either by washing with a solvent or by vacuum drying.

Figure 3A:
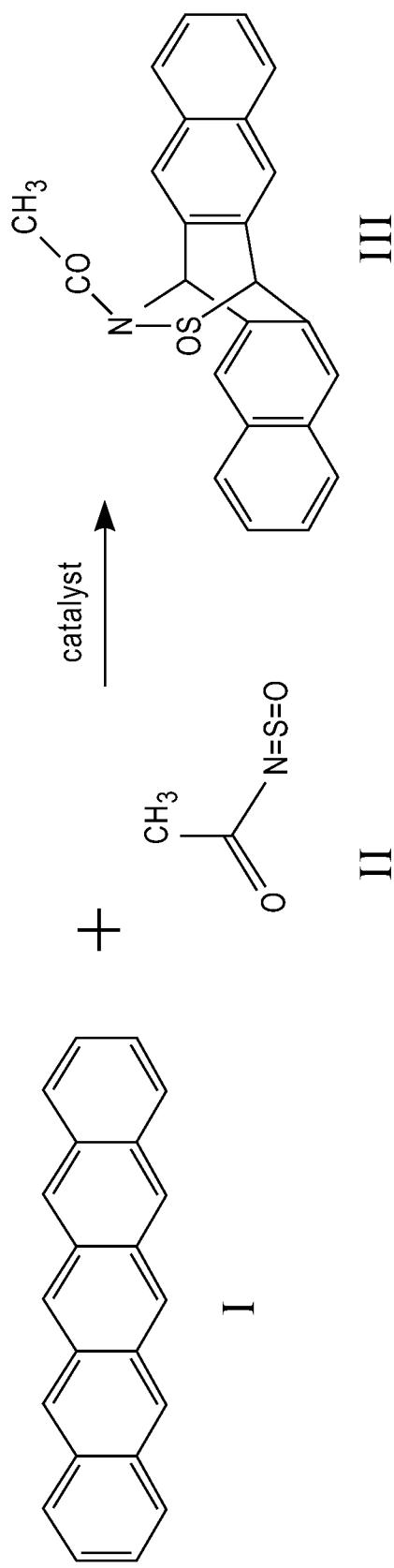
FIG. 3A illustrates pentacene (I) being reacted with the dienophile N-sulfinyl acetamide (II) in the presence of a Lewis acid catalyst to give the pentacene precursor (III), according to an exemplary aspect of the present invention.

FIG. 3A illustrates a reaction (e.g., a Diels-Alder reaction) in which pentacene (I) is reacted with the dienophile N-sulfinyl acetamide (II) in the presence of a Lewis acid catalyst to give the pentacene precursor (III), according to an exemplary embodiment of the present invention.

Forming the Carbon Nanotubes

The carbon nanotubes (CNTs) of the present invention may be formed by any one of several processes including, for example, arc discharge, laser ablation, high pressure carbon monoxide (HiPCO), and chemical vapor deposition (CVD) (e.g., plasma enhanced CVD).

For example, using CVD, a metal catalyst layer of metal catalyst (e.g., including nickel, cobalt, iron, or a combination thereof), is formed on a substrate (e.g., silicon). The metal nanoparticles may be mixed with a catalyst support (e.g., MgO, $Al_2O_3$, etc) to increase the specific surface area for higher yield of the catalytic reaction of the carbon feedstock with the metal particles. The diameters of the nanotubes that are to be grown may be controlled by controlling the size of the metal particles, such as by patterned (or masked) deposition of the metal, annealing, or by plasma etching of a metal layer.

The substrate including the metal catalyst layer may be heated to approximately 700° C. The growth of the CNTs may then be initiated at the site of the metal catalyst by introducing at least two gases into the reactor: a process gas (e.g., ammonia, nitrogen, hydrogen or a mixture of these) and a carbon-containing gas (e.g., acetylene, ethylene, ethanol, methane or a mixture of these).

A plasma may be also be used to enhance the growth process (plasma enhanced chemical vapor deposition), in which case the nanotube growth may follow the direction of the plasma's electric field. By properly adjusting the geometry of the reactor it is possible to synthesize aligned carbon nanotubes.

Generally, the CNTs of the present invention may be electrically and thermally conductive, and have an essentially uniform diameter which is in a range from 1 μm to 3 μm and a length which is in a range from 1 μm to 10 μm. The CNTs may also be single-walled nanotubes (SWNTs) or multi-walled nanotubes (MWNTs) (e.g., double-walled nanotubes (DWNTs)). The CNTs may also have a zigzag, an armchair, or a chiral arrangement, so long as the resulting CNT-pentacene composite should exhibit good charge carrier mobility (e.g., in the range of 1 $cm^2/V \cdot sec$ to 1000 $cm^2/V \cdot sec$).

The CNTs may also be purified (e.g., by washing in a sodium hypochlorite solution) to remove any contaminants.

Forming a Dispersion of the Pentacene Precursors and CNTs

The pentacene precursor (e.g., obtained from a Diels-Alder reaction of pentacene with an N-sulfinylamide) and the purified carbon nanotubes may be dissolved in a solvent to form a mixture of soluble pentacene precursors and carbon nanotubes.

The solvent may include, for example, chloroform, tetrachloroethane, tetrahydrofuran (THF), toluene, ethyl acetate, methyl ethyl ketone (MEK), dimethyl formamide, dichlorobenzene, propylene glycol monomethyl ether acetate (PGMEA) or mixtures of any of these.

The mixture of purified carbon nanotubes and pentacene-N-sulfinylacetamide in an organic solvent may then be sonicated and centrifuged to remove un-coordinated nanotube as sediment. The supernatant liquid remaining after sonicating/centrifuging may serve as the stable dispersion of pentacene precursors and carbon nanotubes in the present invention.

Depositing the Stable Dispersion

Figure 3B:
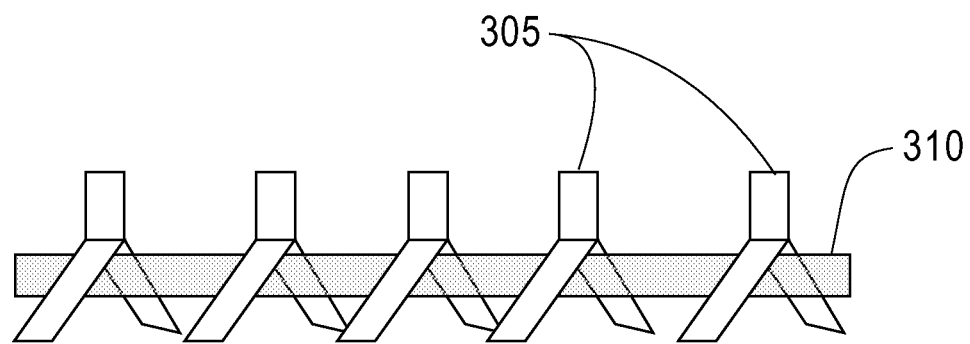
FIG. 3B illustrates an exemplary orientation of the plural molecules of pentacene precursor 305 along the carbon nanotube 310 in the deposited dispersion, according to an exemplary aspect of the present invention.
Figure 3B:
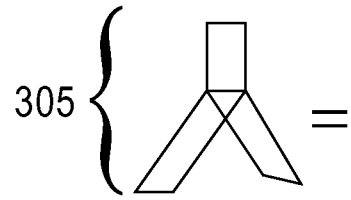
Figure 3B:
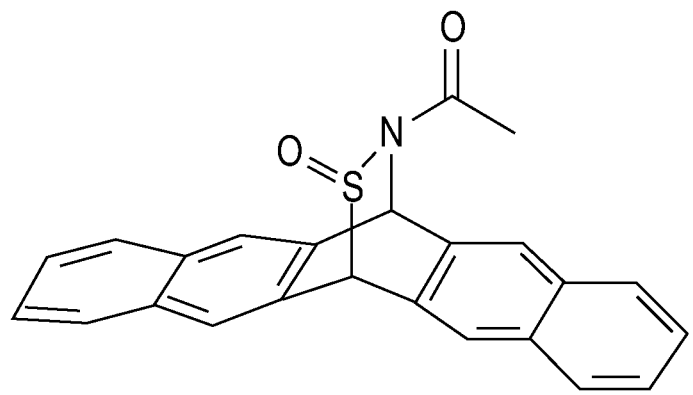

The supernatant liquid may then be deposited on a substrate, for example, by spin coating, drop cast, etc. The supernatant liquid may be deposited, for example, on the substrate at a location which is intended for the CNT-pentacene composite FIG. 3B illustrates an exemplary orientation of the plural molecules of pentacene precursor 305 along the carbon nanotube 310 in the deposited dispersion. As illustrated in FIG. 3B, the molecules of pentacene precursor 305 may include pentacene portions which are formed in a "saddle-like" configuration on the carbon nanotube 310, and N-sulfinyl acetamide functional group portions (e.g., —SO—N—CO—$CH_3$) which are formed at the apex of the "saddle-like" configuration and relatively aligned along the carbon nanotube 310 when viewing the carbon nanotube 310 in an axial direction.

Forming the Composite from the Dispersion

After the stable dispersion of soluble pentacene precursors and carbon nanotubes has been deposited on a substrate, the substrate including the layer of dispersion may be heated at a low temperature (e.g., in a range from 50° C. to 100° C.) to remove the solvent from the layer of dispersion and to form a pentacene precursor coated CNT.

Figure 3C:
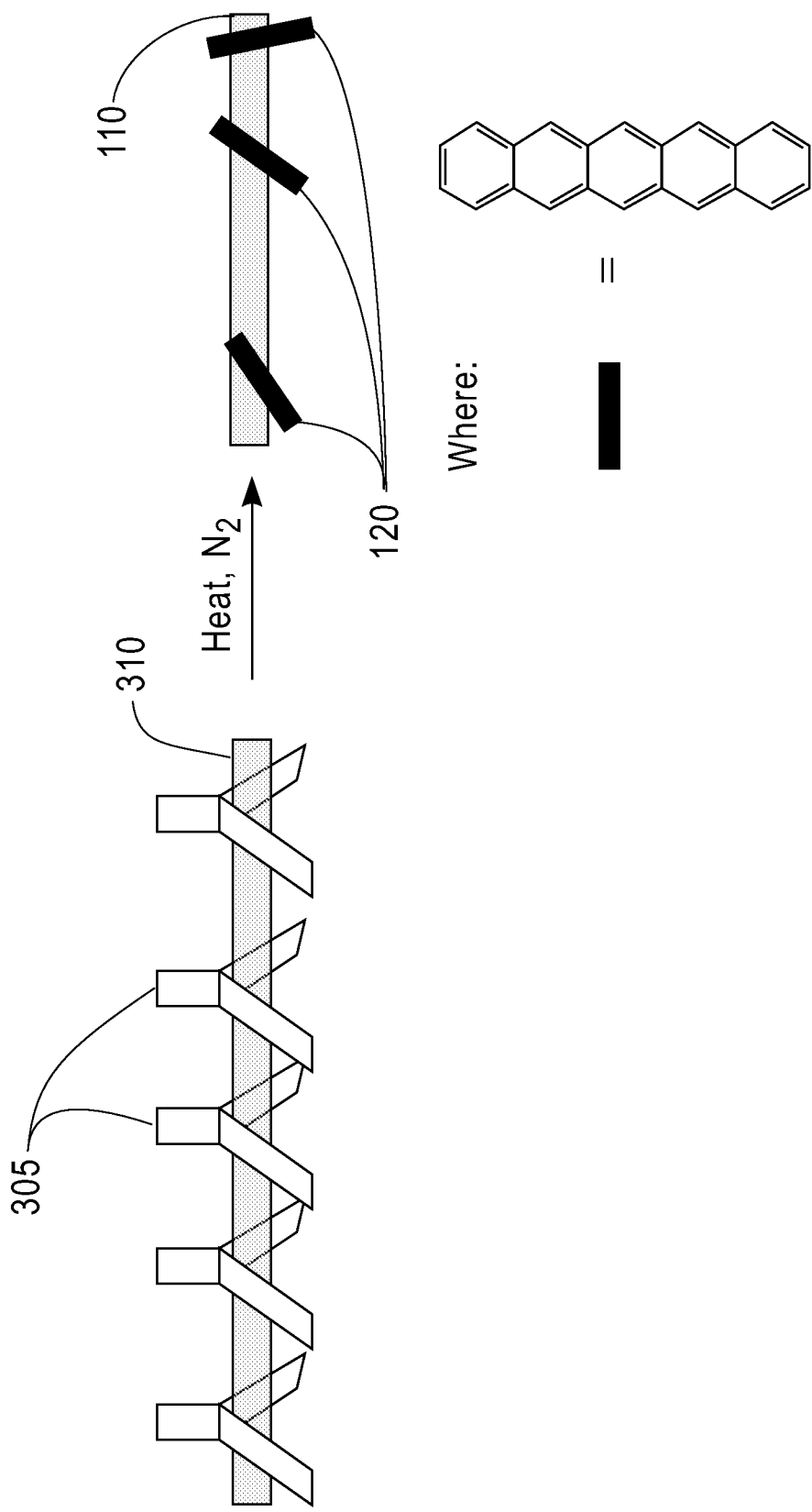
FIG. 3C illustrates heating of the substrate in a nitrogen atmosphere at a temperature in a range from 100° C. to 200° C. to convert the pentacene precursor which is coated on the CNT to pentacene.

As illustrated in FIG. 3C, after removal of the solvent from the layer of dispersion, the substrate may be heated again in a nitrogen atmosphere at a temperature in a range from 100° C. to 200° C. to convert the pentacene precursor which is coated on the CNT to pentacene and, hence, to form a composite of pentacene 120 and carbon nanotube 110 (e.g., CNT-pentacene composite) at a location where the dispersion was deposited.

EXAMPLES

Figure 4:
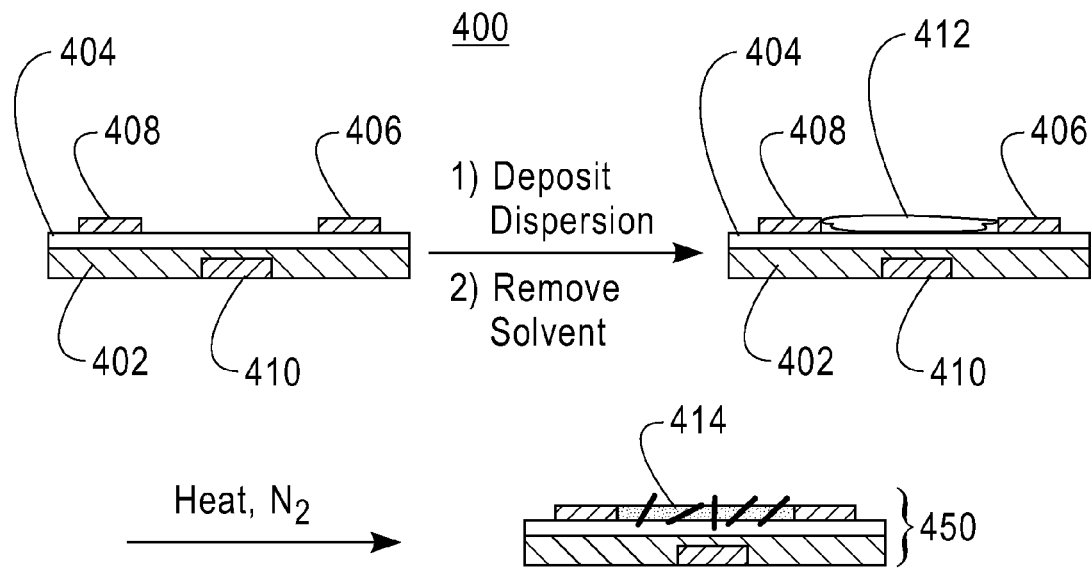
FIG. 4 illustrates an exemplary method 400 of forming a semiconductor device 450 (e.g., field effect transistor (FET)) according an exemplary aspect of the present invention.

FIG. 4 illustrates an exemplary method 400 of forming a semiconductor device 450 (e.g., field effect transistor (FET)) according an exemplary aspect of the present invention.

As illustrated in FIG. 4, a substrate 402 (e.g., semiconductor substrate such as silicon, germanium, etc.) may be provided with a gate electrode 410 (e.g., highly doped silicon), an insulation layer 404 (e.g., SiO$_2$, SiN, SiON), and a source electrode 406 (e.g., gold, palladium, etc.) and a drain electrode 408 (e.g., gold, palladium, etc.) formed on the insulation layer 404 (e.g., gate insulation layer). That is, the substrate 402 may include a predefined source electrode 406, drain electrode 408 and a gate electrode 410.

The dispersion of pentacene precursors and carbon nanotubes may be deposited (e.g., by spin coating, drop cast, etc.) on the insulation layer 404 (e.g., between the source and drain electrodes 406, 408). The solvent is removed (e.g., by heating at low temperature such as in a range from 50° C. to 100° C.) to form the pentacene precursor-coated-CNT 412 on the insulation layer 404 (e.g., between the source and drain electrodes 406, 408), as illustrated in FIG. 4.

After removal of the solvent, the substrate is then heated (e.g., in a range from 100° C. to 200° C.) under nitrogen until all the pentacene precursor decoration are converted to pentacene resulting in a CNT-pentacene composite layer 414 formed on the insulation layer 404 and in the channel area (e.g., between the source and drain electrodes 406, 408). That is, the CNT-pentacene composite layer 414 may serve as the channel material in the device 450. The CNT-pentacene composite layer 414 may have a thickness in a range from 10 nm to 200 nm.

In addition to converting the pentacene precursor-coated-CNT 412 to the CNT-pentacene composite layer 414, the heating may also help to bond the CNT-pentacene composite layer to an adjacent feature (e.g., source and drain electrodes, insulating layer, etc.).

It should be noted that although FIG. 4 illustrates a semiconductor device in which the CNT-pentacene composite layer 414 includes only one carbon nanotube, the composite layer 414 may include plural carbon nanotubes which are coordinated (e.g., aligned) and have plural pentacene molecules formed on each of the carbon nanotubes. In particular, the carbon nanotube(s) in the composite layer 414 may be aligned at least substantially in a direction from one of the source and drain electrodes to the other one of the source and drain electrodes.

It should also be noted that although the FIG. 4 illustrates the device 450 as including the CNT-pentacene composite layer 414 (e.g., channel region) formed on the insulation layer 404 and between the source and drain electrodes 406, 408, other configurations are possible. For example, FIGS. 5A-5C illustrate other possible configurations for the semiconductor device 450 according to other exemplary embodiments of the present invention.

Figure 5A:
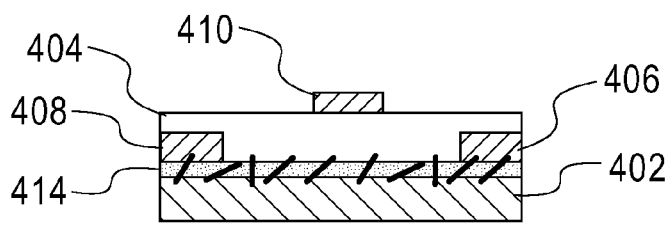
FIGS. 5A-5C illustrate other configurations for the semiconductor device 450, according to other exemplary embodiments of the present invention.

As illustrated in FIG. 5A, the CNT-pentacene composite layer 414 could be formed on the substrate 402, and the source and drain electrodes 406, 408 may be formed on the composite layer 414. The gate insulating layer 404 may then be formed on the source and drain electrodes 406, 408 and the gate electrode 410 may then be formed on the gate insulating layer 404.

Figure 5B:
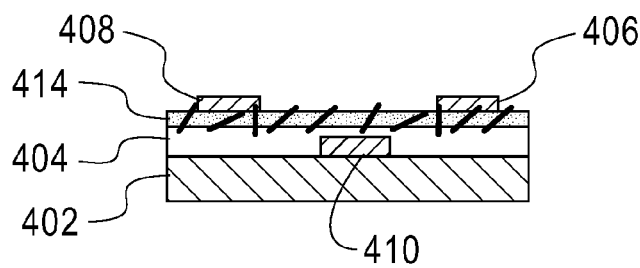

As illustrated in FIG. 5B, the gate electrode 410 may be formed on the substrate 402 and then the gate insulating layer 404 may be formed on the gate electrode 410. The CNT-pentacene composite layer 414 may then be formed on the gate insulating layer 404 and the source and drain electrodes 406, 408 may be formed on the gate insulating layer 404.

Figure 5C:
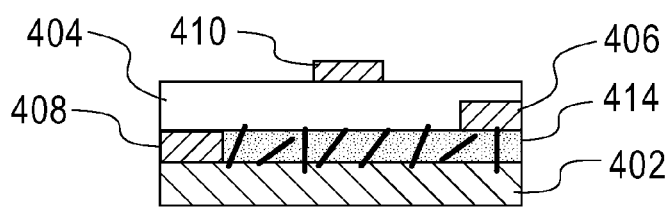

Further, as illustrated in FIG. 5C, the CNT-pentacene composite layer 414 could be formed on the substrate 402, and one of the source and drain electrodes 406, 408 (in this case, the drain electrode) may be formed on the substrate 402 beside the composite layer 414. Then, the other of the source and drain electrodes 406, 408 (in this case, the source electrode) and the gate insulating layer 404 may be formed on the composite layer 414. The gate electrode 410 may then be formed on the gate insulating layer 404.

Figure 6:
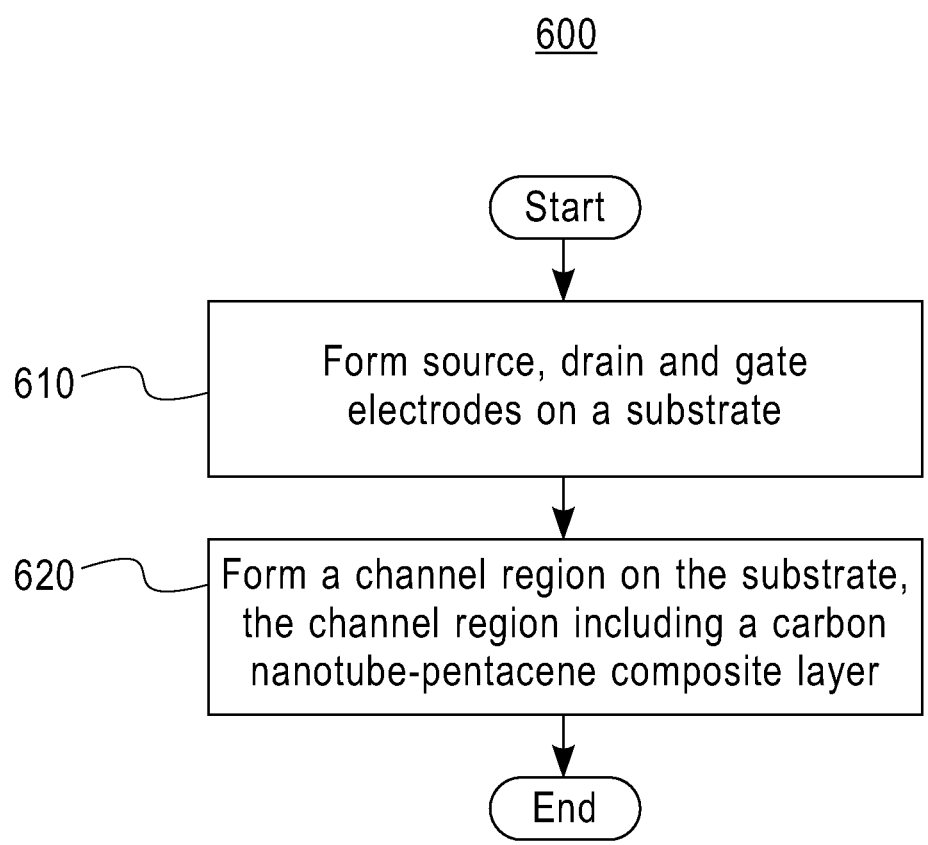
FIG. 6 illustrates an exemplary method 600 of forming a semiconductor device according to the present invention.

FIG. 6 illustrates an exemplary method 600 of forming a semiconductor device according to the present invention. As illustrated in FIG. 6, the method 600 includes forming (610) source, drain and gate electrodes on a substrate, and forming (620) a channel region on the substrate, the channel region including a carbon nanotube-pentacene composite layer.

It should also be noted that although the present invention is described herein as being used to form a transistor, the invention may be used to form other semiconductor devices which utilize a layer having good charge carrier mobility (e.g., diodes, photovoltaics, etc.).

With its unique and novel features, the exemplary aspects of the present invention may provide a method of forming a semiconductor device including forming a channel region including a carbon nanotube-pentacene composite layer.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive assembly is not limited to that disclosed herein but may be modified within the spirit and scope of the present invention.

Further, Applicant's intent is to encompass the equivalents of all claim elements, and no amendment to any claim in the present application should be construed as a disclaimer of any interest in or right to an equivalent of any element or feature of the amended claim.

What is claimed is:

1. A composite material comprising
    a carbon nanotube-pentacene composite comprising:
        a carbon nanotube; and
        plural pentacene molecules bonded to said carbon nanotube,
    wherein said plural pentacene molecules are substantially aligned and formed transversely across a long axis of the carbon nanotube, and interact with a sidewall of the carbon nanotube through $\pi$-$\pi$ stacking,
    wherein the carbon nanotube-pentacene composite comprises a charge carrier mobility in a range from 1 cm$^2$/V·sec to 1000 cm$^2$/V·sec.

2. The composite material of claim 1, wherein said plural pentacene molecules are bonded to said carbon nanotube by $\pi$-$\pi$ bonding, charge-transfer bonding and electrostatic bonding.

3. The composite material of claim 1, wherein said carbon nanotube comprises an electrically semiconductive, single-walled carbon nanotube.

4. The composite material of claim 1, wherein said plural pentacene molecules are bonded to said carbon nanotube by charge-transfer bonding.

5. The composite material of claim 1, wherein said plural pentacene molecules are bonded to said carbon nanotube by electrostatic bonding.

6. The composite material of claim 1, wherein the plural pentacene molecules interact with a graphitic sidewall of the carbon nanotube and align on the sidewall of the carbon nanotube through $\pi$-$\pi$ stacking.

7. The composite material of claim 1, wherein rings of the plural pentacene molecules form stacks with rings of the carbon nanotube.

8. The composite material of claim 1, wherein the plural pentacene molecules are bonded to an outer surface of the carbon nanotube such that double bonds of the carbon nanotube are substantially unaffected by the plural pentacene molecules, thereby ensuring that electrical and mechanical properties of the carbon nanotube are unaffected by the plural pentacene molecules.

9. The composite material of claim 1, wherein the plural pentacene molecules are formed transversely across the long axis of the carbon nanotube, such that a molecular axis of the plural pentacene molecules is substantially perpendicular to the long axis of the carbon nanotube.

10. A composite material layer comprising:
a layer of carbon nanotube-pentacene composite material comprising:
  a plurality of carbon nanotubes which are substantially aligned; and
  plural pentacene molecules bonded to the plurality of carbon nanotubes,
wherein the plural pentacene molecules are substantially aligned and formed transversely across a long axis of the plurality of carbon nanotubes, and interact with a sidewall of the plurality of carbon nanotubes through π-π stacking,
wherein the carbon nanotube-pentacene composite material comprises a charge carrier mobility in a range from 1 $cm^2$/V·sec to 1000 $cm^2$/V·sec.

11. The layer of claim 10, wherein the layer of carbon nanotube-pentacene composite material has as thickness in a range from 10 nm to 200 nm.

12. The layer of claim 10, wherein the layer of carbon nanotube-pentacene composite material comprises a channel layer of a field effect transistor.

13. A device comprising:
a substrate;
a gate insulation layer formed on the substrate;
a gate electrode formed on the gate insulation layer; and
a carbon nanotube-pentacene composite layer which is formed on the substrate such that the gate insulation layer is formed between the gate electrode and the carbon nanotube-pentacene composite layer, the carbon nanotube-pentacene composite layer serving as a channel layer and comprising:
  a plurality of carbon nanotubes which are substantially aligned; and
  plural pentacene molecules bonded to the plurality of carbon nanotubes,
wherein the plural pentacene molecules are substantially aligned and formed transversely across a long axis of the plurality of carbon nanotubes, and interact with a sidewall of the plurality of carbon nanotubes through π-π stacking, and
wherein the carbon nanotube-pentacene composite comprises a charge carrier mobility in a range from 1 $cm^2$/V·sec to 1000 $cm^2$/V·sec.

14. The device of claim 13, wherein the device comprises one of a field effect transistor (FET) a diode and a photovoltaic cell.

15. The device of claim 13, further comprising:
source and drain electrodes formed on the substrate,
wherein the plurality of carbon nanotubes are aligned at least substantially in a direction from one electrode of the source and drain electrodes to the other electrode of the source and drain electrodes.

16. The device of claim 13, wherein the carbon nanotube-pentacene composite layer comprises a thickness in a range from 10 nm to 200 nm.

* * * * *